United States Patent [19]
Taylor et al.

[11] Patent Number: 5,933,228
[45] Date of Patent: Aug. 3, 1999

[54] INTEGRAL IMAGING LENS SHEETS

[75] Inventors: Roy Y. Taylor, Scottsville; Roland L. Williams, Rochester, both of N.Y.

[73] Assignee: Eastman Kodak Company, Rochester, N.Y.

[21] Appl. No.: 08/866,880

[22] Filed: May 30, 1997

[51] Int. Cl.[6] .......................... G01N 21/88; G02B 27/10
[52] U.S. Cl. ...................... 356/124; 359/619; 356/125
[58] Field of Search .................................. 359/619, 626, 359/627; 356/124, 125, 127

[56] References Cited

U.S. PATENT DOCUMENTS

| | | | |
|---|---|---|---|
| 3,912,395 | 10/1975 | Voggenthaler | 356/124 |
| 4,033,696 | 7/1977 | Nohda | 356/126 |
| 5,321,493 | 6/1994 | Kamon | 356/124 |
| 5,554,432 | 9/1996 | Sandor et al. | 428/157 |

*Primary Examiner*—Robert H. Kim
*Assistant Examiner*—Zandra V. Smith
*Attorney, Agent, or Firm*—William F. Noval

[57] ABSTRACT

A method, and apparatus and lens sheet manufacturing process which utilize the method, of evaluating the quality of a lenticular lens sheet having a front side carrying a plurality of elongated parallel lens elements, and a back side. The method includes:

(a) illuminating the sheet from one of the sides with a light source so that the light passes through the sheet and is then reflected from a reflector behind the other side to pass back through the sheet; and (b) comparing an observed feature of a pattern of the reflected light which has passed back through the sheet with a corresponding reference feature to provide an indication of the lenticular lens sheet quality.

22 Claims, 7 Drawing Sheets

INTEGRAL IMAGING LENS SHEETS

FIELD OF THE INVENTION

This invention relates to the field of integral imaging, and lenticular imaging in particular, and the manufacture of lens sheets used in such imaging.

BACKGROUND OF THE INVENTION

Integral image elements which use a lenticular lens sheet or a fly's eye lens sheet, and a three-dimensional integral image aligned with the sheet, so that a user can view the three-dimensional image without any special glasses or other equipment, are known. Such imaging elements and their construction, are described in "Three-Dimensional Imaging Techniques" by Takanori Okoshi, Academic Press, Inc., New York, 1976. Integral image elements having a lenticular lens sheet (that is, a sheet with a plurality of adjacent, parallel, elongated, and partially cylindrical lenses) are also described in the following Unites States patents: U.S. Pat. No. 5,391,254; U.S. Pat. No. 5,424,533; U.S. Pat. No. 5,241,608; U.S. Pat. No. 5,455,689; U.S. Pat. No. 5,276,478; U.S. Pat. No. 5,391,254; U.S. Pat. No. 5,424,533 and others; as well as allowed U.S. patent application Ser. No. 07/931,744. Integral image elements with lenticular lens sheets use interlaced vertical image slices which, in the case of a three-dimensional integral image, are aligned with the lenticules so that a three-dimensional image is viewable when the lenticules are vertically oriented with respect to a viewer's eyes. Similar integral image elements, such as described in U.S. Pat. No. 3,268,238 and U.S. Pat. No. 3,538,632, can be used to convey a number of individual two-dimensional scenes (such as unrelated scenes or a sequence of scenes depicting motion) rather than one or more three-dimensional images.

Integral image elements using reflective layers behind the integral image to enhance viewing of the integral image by reflected light, are also described in U.S. Pat. No. 3,751,258, U.S. Pat. No. 2,500,511, U.S. Pat. No. 2,039,648, U.S. Pat. No. 1,918,705 and GB 492,186.

In a typical method of assembling a lenticular type of integral image element, an original negative is exposed from stored digitized data of a composite lenticular image on a film writer. A suitable film writer is the Symbolic Sciences International Fire 1000 and the LVT Model 1620B, available from Light Valve Technology, a subsidiary of Eastman Kodak Company, Rochester, N.Y. A suitable negative exposure technique is disclosed in U.S. Pat. No. 5,276,478. After photographic processing, the negative is printed, typically by a projection enlarger, onto a suitable film- or paper-based photographic print stock. After processing, the lenticular composite print is coated with adhesive, aligned with a lenticular lens sheet, and pressed against the lens sheet to permanently adhere to it in proper registration with the printed lenticular composite image. However, it is also known to write the lenticular image directly onto a back side of a lenticular lens sheet which is coated with a suitable receiving layer, such as disclosed in U.S. Pat. No. 5,349,419 and U.S. Pat. No. 5,279,912. Furthermore, such "writing" of the lenticular image can be temporary, as in a display produced on a CRT or Liquid Crystal Display ("LCD") screen immediately adjacent the back side. There are indications that lenticular imagery may increasingly be applied to LCD screens and the like to make effective 3D video a commercial reality.

Typically, in manufacturing a lenticular lens sheet a hot plastic melt composition is contacted with a hollow drum carrying a series of adjacent, concave, grooves of semicircular transverse cross-section, along the length of its cylindrical surface. The drum is heated to a controlled temperature by water flow therethrough. Hot plastic composition cools on the rotating drum surface to form a continuous lenticular lens sheet with the lens elements extending along the direction of the continuous lens sheet. Such techniques are well known in the art of forming lenticular lens sheets. However, in other methods the grooves can be along the length of the cylinder, so that the final lenticules formed in the continuous lens sheet are oriented across the lens sheet. Since each of the lenses of a lenticular lens sheet is dedicated to one or more corresponding sets of interleaved image lines, it is important during manufacture of a continuous lens sheet or multiple individual lens sheets, that the lenticular lens sheet be of well controlled quality. Variations in lens pitch (which for the usual case of immediately adjacent lenses, is equal to the lens width) will result in inaccurate matching of individual lenses with corresponding line sets and consequently poor images when viewed. Similarly, the lens sheet thickness should remain relatively constant so that the image lines will be positioned at the individual lens focal points (whether this is as a result of being positioned directly on the back side of the lens sheet or being separated therefrom). Other lens characteristics such as refractive index of the plastic material, and lens shape (affecting image display geometry and image ghosting), should also preferably remain relatively constant. However, one or more of these parameters may vary during manufacture of a continuous lens sheet as a result of changes in the temperature of the roller or the composition being fed in, flow rates of the hot plastic composition or variations in roller speed.

The ability to produce high quality lenticular lens sheets has always been a definite factor in the commercial feasibility of all types of lenticular imagery. In current techniques, the image quality of lenticular optics is typically postevaluated with a microscope, the thickness measured with micrometers, the pitch measured with optical comparators, the surface profiles traced with profilometers, and index variations can be assessed with immersion refractometry and interferometry. However, none of these techniques has been successful in evaluating the optical performance in a way directly analogous to the eventual assembly performance with the printed image. Additionally, none of these techniques readily lend themselves to high volume production of a continuous lens sheet or individual lens sheets, where the lens sheet characteristics need to be measured rapidly so that incorrect conditions which result in poor quality lens sheets can be corrected before further incorrect lens sheet material is formed. The control of thickness in an extrusion process can be monitored with scanning atomic radiation devices and feedback signals can be used to vary certain extrusion parameters affecting thickness. However, a question always remains of whether the nominal thickness being maintained is the correct thickness for lenticular performance in the assembly application (in which an image is aligned with the lens sheet). That is, the measurement itself is not directly related to the manner of use of the lens sheet.

It would be desirable then, to have a means for assessing the quality of a lenticular lens sheet, in particular one or more of the parameters described above, which is rapid to allow its application to high volume production of lens sheet and which provides indications of quality which are related to the manner of use of the lens sheet.

SUMMARY OF THE INVENTION

The present invention then, provides in one aspect, a method of evaluating the quality of a lenticular lens sheet having a front side carrying a plurality of elongated parallel lens elements, and a back side, comprising:

(a) illuminating the sheet from one of the sides with a collimated light source so that the light passes through the sheet and is then reflected from a reflector behind the other side to pass back through the sheet; and (b) comparing an observed feature of a pattern of the reflected light which has passed back through the sheet with a corresponding reference feature to provide an indication of the lenticular lens sheet quality.

In another aspect of the present invention, the method comprises:

(a) illuminating the sheet from the front side with a collimated light source so that the light passes through the sheet and is then reflected from a reflector behind the back side to pass back through the sheet;

(b) comparing an observed feature of a pattern of the reflected light which has passed back through the sheet with a corresponding first reference feature to provide an indication of the lenticular lens sheet quality;

(c) illuminating the sheet from the back side with a collimated light source so that the light passes through the sheet and is then reflected from a reflector forward of the front side to pass back through the sheet; and (d) comparing an observed feature of a pattern of the reflected light which has passed back through the sheet with a corresponding second reference feature to provide an indication of the lenticular lens sheet quality.

A method of manufacturing lenticular lens sheets using the foregoing evaluation method, and a lenticular lens sheet manufacturing apparatus using the foregoing method, are also provided.

The present invention provides for the assessment of the quality of a lenticular lens sheet, in a manner which can be made relatively rapid to allow its application to high volume production of lens sheet, and which provides indications of quality which are related to the manner of use of the lens sheet.

BRIEF DESCRIPTION OF THE DRAWINGS

To facilitate understanding, identical reference numerals have been used, where possible, to designate identical elements that are common to the figures.

DETAILED DESCRIPTION OF THE INVENTION

It will be appreciated in the present invention, that the lenticular lens sheet could more generally be an "integral" lens sheet (which would include a fly's eye lens sheet). While a lenticular lens sheet typically has a front side on which the curved surfaces of the elongated parallel lens elements (typically partially or semi-cylindrical in transverse cross section) are formed, the lens elements could alternatively be formed of regions of varying indices of refraction through the volume of the lens sheet, which are configured in such a way as to provide (in conjunction with the surfaces of the sheet, such as a curved external surface, flat external surface or some other shape) the same optical deflection of light rays as would be provided by a conventional lenticular lens sheet. Ways of constructing such lenticular and fly's eye lens sheets are well known and include extrusion and compression molding techniques. Also, the back surface of the lens sheet may also be curved (such as convexly) so as to either strengthen the lens effect or compensate for the curved focal plane which may be inherent in the lens construction. Consequently, the curvature on the back side may be of such a shape as to match the curvature of the focal plane of the lens. Further, by an "integral composite image" is referenced an image composed of segments (interlaced lines, in the case of a "lenticular composite image") from at least one complete image (and often more than one image), which segments are aligned with respective individual lenses so that each of the one or more images is viewable when a user's eyes are at the correct angle relative to the imaging element. An integral lens web may be a continuous web of any integral element lens sheet type.

It will be appreciated throughout this application, by a "processor" is referenced a suitable signal processor, such as a suitably programmed general purpose digital processor or hard wired equivalent circuitry. As to the receiving medium on which the integral image is written, this can simply be the back side of the integral lens sheet (which in a conventional integral lens sheet is opposite the shaped lens surfaces or equivalents, such as the semi-cylindrical shaped lens surfaces of a lenticular lens sheet). Alternatively, the image receiving medium could be one or more layers coated on the back side, such as a photosensitive layer or layers (which may in particular be any known photographic layer or layers). Alternatively, a transparent substrate bearing one or more photographic layers or other writable image bearing layers using thermal or inkjet or electrophotographic methods (such as the transparent base of a conventional photographic film) may attached either before or after the image is written thereon, to a lenticular lens sheet by adhering the transparent substrate to the back side of the lens sheet (with either the image bearing layer or transparent base being directly adhered to the back side of the lens sheet, or alternatively with a transparent spacer being positioned between the lens sheet and the substrate). Of course, the image bearing layer can be spaced from the back side of a lens sheet by any means, such as by an air gap or a transparent optical sheet. This construction can be taken into account in evaluating lens sheet thickness using the method of the present invention. Additionally, the image receiving medium on the back side, can be covered with a protective layer either before or after writing the image. In the case of such a protective layer covering before writing the image, the protective layer can be transparent so that writing can be done by a light beam illuminating photosensitive layers on the back side. It will also be appreciated that the methods of the present invention can be applied to integral images (and particularly lenticular images) which can exhibit a wide range of effects including motion, depth, flip, and other lenticular related effects.

Figure 1:
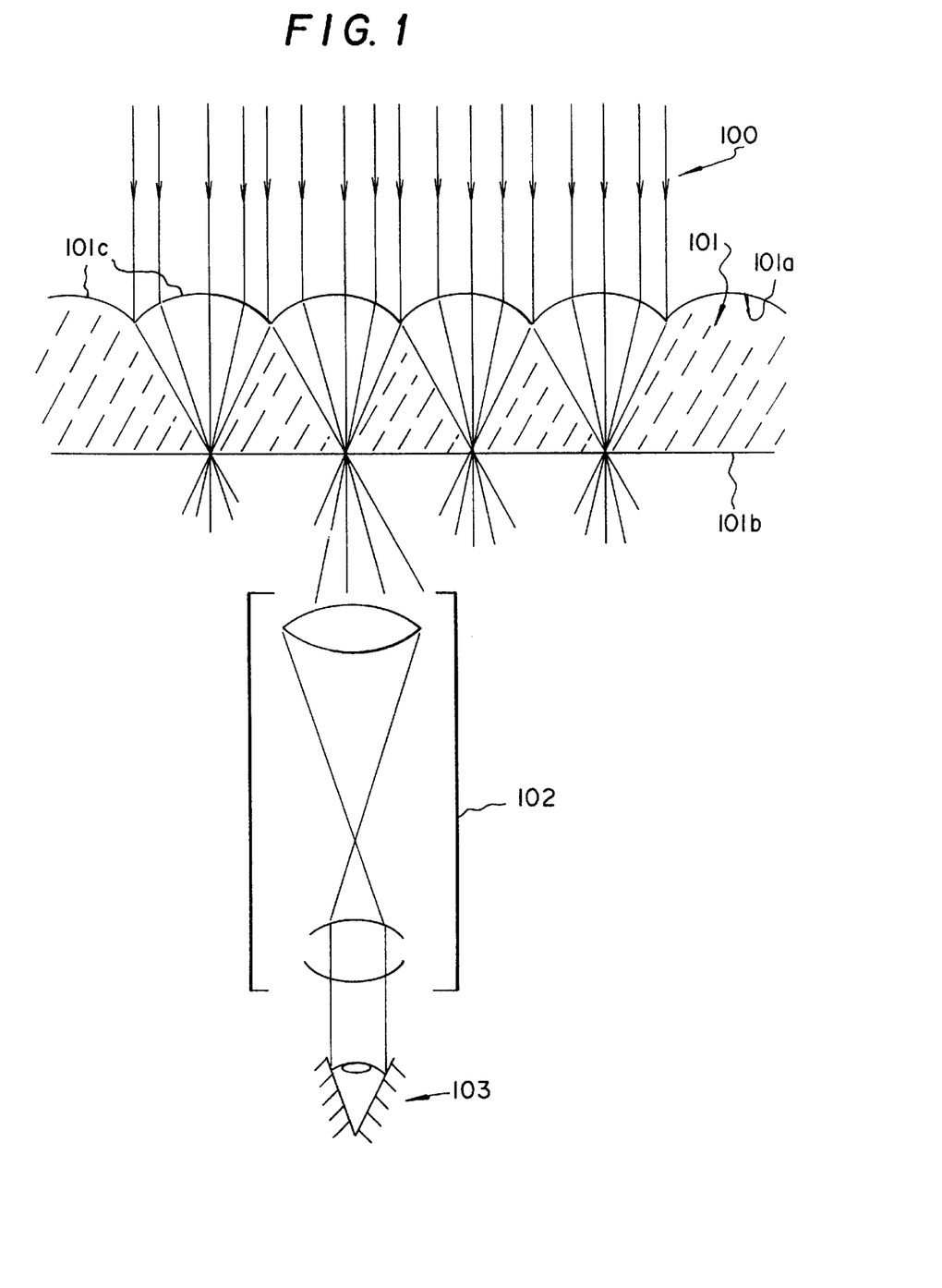
FIG. 1 illustrates a prior art method of evaluating a lenticular lens sheet parameter.

In the prior art system illustrated in FIG. 1, a collimated beam of light 100 is directed at a lenticular sheet 101 from a front side 101a of sheet 101. Front side 101a carries a plurality of elongated, parallel, nominally cylindrical lenses (known as "lenticules") which are viewed in transverse cross-section in FIG. 1. Lens sheet 101 also has a planar back side 101b. The effect of the curved cylindrical surface is to focus the beam to small lines of light near the second surface of the sheet (extending into the page as viewed in FIG. 1). The surface 101b is the location to which the printed composite image will be joined by lamination or physical clamping. A microscope 102 is positioned to focus on a line of the line pattern. The quality of the lenticular image is visually assessed by a user's eye 103 observing through the microscope 102 and evaluating or measuring the lateral spread of light in a direction normal to the cylindrical axis. The position of the microscope can also be adjusted toward and away from the back side 101b to find the position of minimal line spread. This can be used to determine if the sheet is the proper thickness for locating the printed composite image, taking into account other considerations such as adhesive thickness, image overcoating thickness, and the thickness of a transparent spacer (if any).

Figure 2:
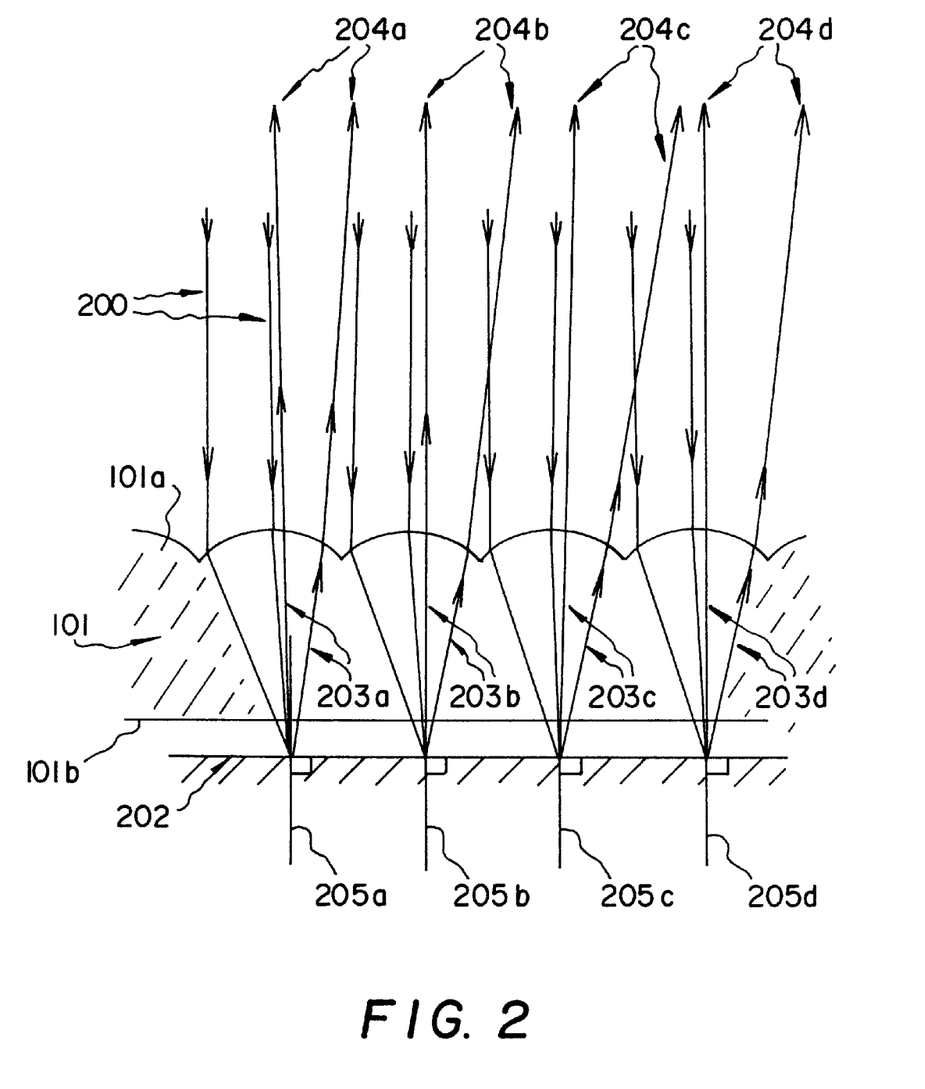
FIG. 2 illustrates a method of the present invention.

In the method of the present invention shown in FIG. 2, a collimated light beam 200 is directed at the sheet 101 as before. The microscope is replaced by a flat reflective surface 202 which causes rays of light 203a, 203b, 203c, 203d from adjacent lenticules to be reflected back toward the curved surfaces of the adjacent lenticules in lenticular sheet 101 on paths which are at angles symmetric about normals 205a, 205b, 205c, 205d to the reflective surface. The reflective surface is made parallel to back side 101b by means of fixturing (that is, something to hold the reflective surface in place) and spaced therefrom by an amount sufficient equal to the spacing, if any, of the composite image from the back side 101b (such as allowing for adhesive thickness and optical field curvature of the lenticule, as well as the thickness of any transparent spacer between the image and the lens sheet). If the reflective surface 202 has been located in this fashion at the focal plane of the lenticules, the rays will again be refracted to a nominally parallel beam condition except when errors in the curved surfaces of the lenticules or variations in the refractive index of the sheet material occur. If these errors exist, the rays emerging 204a, 204b, 204c, 204d from the lenticular sheet following this reflection and refraction will not be exactly parallel to each other, but either fanning out in a converging or diverging fashion.

It is possible to evaluate such an emerging beam by autocollimator techniques long known in the art of optical meteorology. In this case a resolution target is converted to the input collimated beam by an optical collimator lens and the reflected/returned beam is intercepted by the same lens and directed to an eyepiece for visual assessment of the resolution target image, or to a sensor for electronic assessment of the modulation transfer function. However, the image resolution evaluated by this method does not predict the functional characteristics of the lenticular sheet which is to project minute lines of a recorded image into discrete collimated paths.

Figures 3, 4:
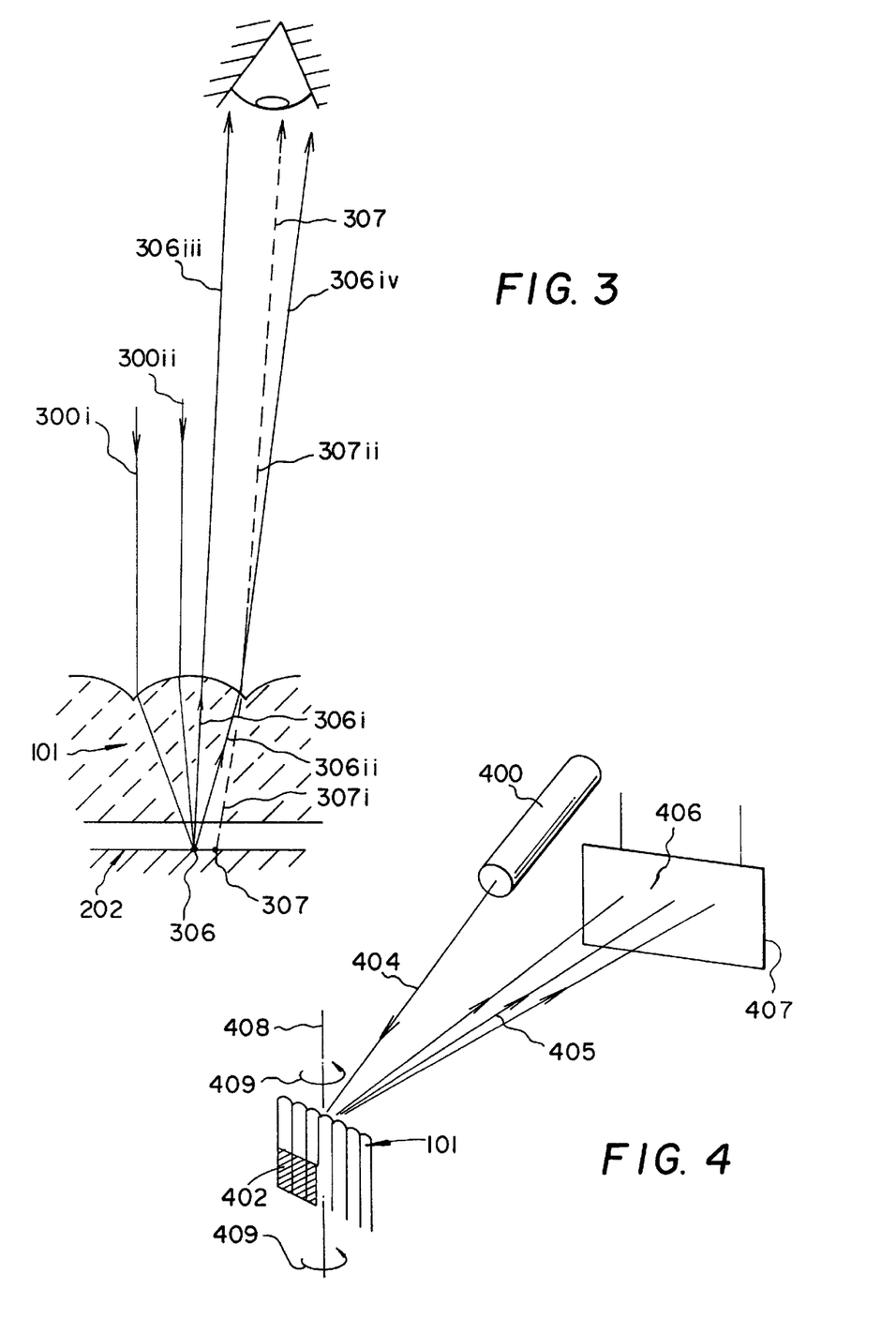
FIG. 3 illustrates a spreading effect due to incorrect thickness of a lenticular lens sheet.
FIG. 4 illustrates an apparatus of the present invention.

The purpose of the lenticular sheet is to assure that the information visible at a given viewing location comes from only one line for each lenticule in the composite image. FIG. 3 illustrates what will happen when the thickness of the lenticular sheet 101 is incorrect (in the case of FIG. 3, sheet 101 is too thin). In FIG. 3 (wherein incoming light paths are designated by 300i, 300ii) the information from line 307 traveling along paths 307i and 307ii is superimposed by part of the light from line 306 traveling along the paths 306i and 306iii, respectively because 306iii and 307ii are parallel (whereas paths 306iii and 306iv are diverging). This condition is called ghosting. The effect of ghosting is to reduce the purity of the color seen over the full lateral aperture of any lenticule.

In the embodiment shown in FIG. 4, the collimated beam 404 is provided by a helium-neon type laser 400, but any wavelength laser will suffice with an appropriate sensor. Beam 404 preferably has a width at least equal to or greater than the lenticular pitch and, as shown in FIG. 4 may have a width equal to several times that of the lenticular pitch. A planar reflector 402 is located behind and parallel to the back surface 101b and held there by suitable mechanical means. The back side 101b of the lenticular sheet 101 is oriented so that its lenticule axes extend in a vertical direction as viewed in FIG. 4. The reflected beam 405 produces an observed pattern 406 on a screen 407. Screen 407 may be planar as shown, or may be curved laterally in a cylindrical manner (concave side facing lens sheet 101) about the interception of the laser beam 400 with lenticular sheet 101. The collimated light from laser 400 is directed within a plane normal to the sheet and parallel to the axes of the lenticules. The center of observed pattern 406 will be found to coincide with the interception of this plane and screen 407. The width of the pattern on screen 407 can serve as a quality parameter which can be compared with a corresponding reference parameter. From the foregoing discussion, a "perfect" pattern would be a spot equal in width to that of the input beam 404 (the value of such width serving as a reference parameter). However, due to errors in the lenticular sheet thickness and lenticule radius of curvature, the pattern will typically spread out laterally (in this illustration, horizontally). Alternatively, rather than measuring a width of pattern 406 when sheet 101 is held still, sheet 101 can be pivoted over a fixed angle in the direction of arrows 409 about a central axis 408 of the sheet. The data from the arrangement of FIG. 4 is particularly useful in assessing whether the thickness of lens sheet 101 is correct. Once pattern 406 has been evaluated (in particular, when the pattern width has been minimized) at one location on sheet 101, sheet 101 can be relocated while reflector 402 is held a fixed distance from sheet 101, so that light from laser 400 strikes a different part of sheet 101. Multiple locations on sheet 101 can be tested in this way as a measure of uniformity of sheet 101. Alternatively, rather than moving sheet 101, the components of FIG. 4 other than sheet 101 can be moved as a unit to obtain the effect of testing multiple locations on sheet 101 for uniformity of lens sheet thickness.

The principal sources of optical performance degradation of the lenticular lens sheet are: 1) thickness of the sheet or lenticule curvature is incorrect, causing the reflecting surface to be placed at the wrong location; 2) the curvature of the cylindrical surface is not consistent over the aperture, causing a wide pattern spread, regardless of the sheet thickness; 3) the plastic material has striations (or localized index of refraction variations), causing spiked variations in the pattern brightness (that is "hot spots" in brightness). Therefore, to enable to more accurate control of lens sheet quality, of a lens sheet formed by a lens sheet forming apparatus, further data is useful.

Figure 5A:
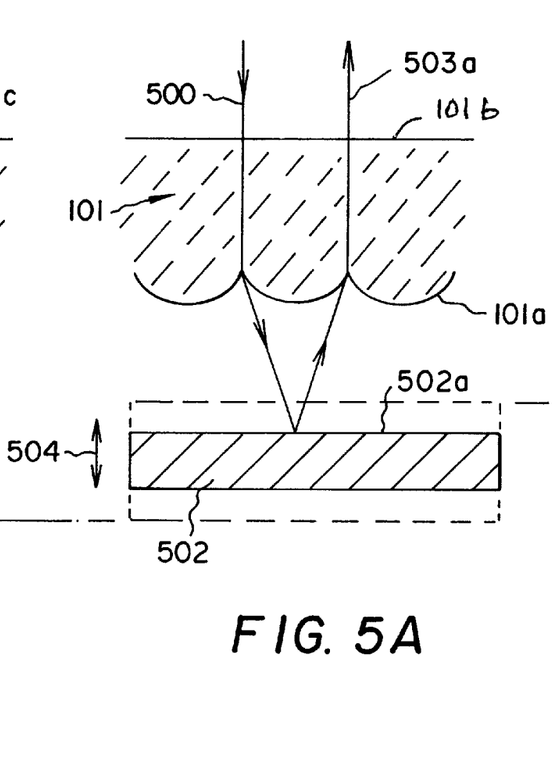
FIGS. 5A through 5C illustrate an alternate method of the present invention.
Figure 5B:
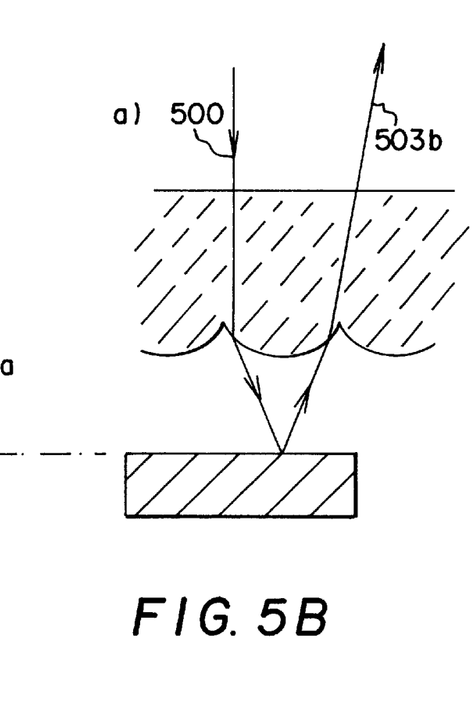
Figure 5C:
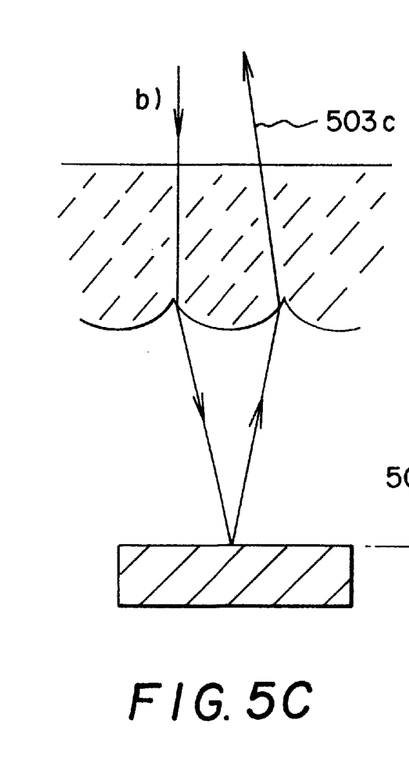

FIGS. 5A to 5C illustrate a way of providing an evaluation of errors in the shape of lens surfaces 101c. The method illustrated in FIGS. 5A to 5C can be used independently, or preferably, in conjunction with the method described in relation to FIG. 4. In FIG. 5A the collimated beam including ray 500 is directed toward the lenticular sheet 101 from the flat side back side 101b. The collimated beam is directed in a plane normal to the sheet and parallel to the axis of the lenticules. The reflector 502 causes a reflected beam of which ray 503a (FIG. 5A) is one component, to reflect off its front surface 502a. Reflector 502 is provided with an oscillating motion in a direction 504 normal to the reflector surface. As the reflector 502 is moved closer to lens sheet 101 as shown in FIG. 5B, the ray 503b will be directed at an angle diverging away from the direction of ray 500. As the reflector 502 location is moved away from lens sheet 101 as shown in FIG. 5C, the ray 503c will be directed at an angle converging across the direction of ray 500. The cumulative effect of all the rays from the input beam is to cause a variation in the spread of the pattern on a screen set up in a manner similar to that described in FIG. 4.

It should be understood that the movement of reflector 502 back and forth in the direction 504 as seen in FIG. 5A, can be accomplished by an oscillating motion from a mechanical oscillator through a practical range. The position of reflector 502 relative to the front surface 101a can be sensed and correlated with the reflected pattern obtained to determine the position where the minimal dispersed pattern occurs, which could then be used to provide a signal useful for predicting the thickness the lenticular sheet should be made to correctly display the image for which it is intended bearing in mind any intended spacing of the image from the lens sheet. Errors in the width of the pattern seen in FIG. 5 result from forming variables causing a greater or less amount of lens curvature upon cooling. These categories of errors are correctable by controlling different process variables during forming of the lens sheet. The width of the pattern (which serves as an observed feature) can be evaluated as a function of the location of the reflecting surface 502a and a decision made as to whether the pattern is small enough at some location of surface 502a. If so, this location can be used to indicate a desired change in lens sheet 101 thickness to result in an acceptable pattern resulting from the test of FIG. 4. If not, other lens sheet forming variables that affect lens curvature can be adjusted to make the pattern smaller. Furthermore, the distribution of light intensity across the pattern on the screen during the reflector oscillation cycle can also be evaluated to determine if the irregularities of the curvature and the internal index striations is causing non-uniform "hot spots" in the spread. In this case, the chill roller used to form the lens sheet, or the material used for forming the lens sheet 101, should be checked for contamination. Similar to the technique discussed above in connection with FIG. 4, once the resulting pattern has been evaluated (in particular, when the pattern width has been minimized) at one location on sheet 101, sheet 101 can be relocated while reflector 502 is held a fixed distance from sheet 101, so that light from a laser strikes a different part of sheet 101. Multiple locations on sheet 101 can be tested in this way as a measure of uniformity of sheet 101. Alternatively, rather than moving sheet 101, the components of the system other than sheet 101 can be moved as a unit to obtain the effect of testing multiple locations on sheet 101 for uniformity of expected image quality.

Lens sheet forming machines typically incorporate a thickness measuring device such as a radiation attenuation sensors for monitoring the physical thickness of the formed sheet. Such a device can be used in a method and apparatus of the present invention to ensure that any physical thickness adjustment, as described above, stays within a predetermined acceptable range.

Figure 6:
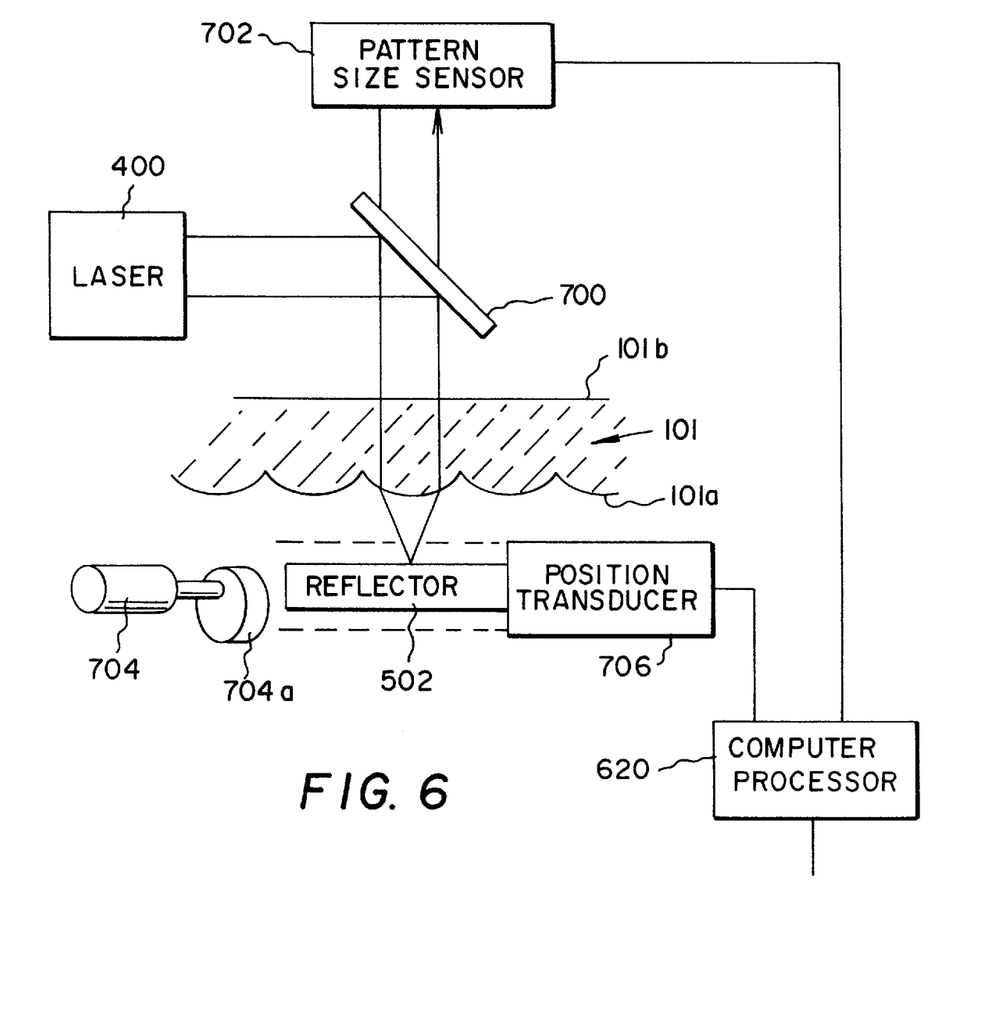
FIG. 6 is a schematic diagram showing a particular apparatus for executing the method shown in FIGS. 5A–5C.
Figure 7:
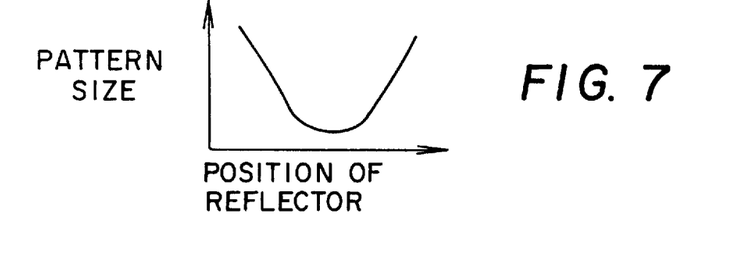
FIG. 7 is a graph of a signal output by the apparatus of FIG. 6.

Referring to FIG. 6, there is shown a practical apparatus for implementing the method illustrated in FIG. 5. The apparatus shown laser 400 produces a collimated light beam which is reflected by beam splitter 700 toward lens sheet 101, intercepting sheet 101 at the flat back side 101b first. The front side 101a focuses the beam to a line. Reciprocal motion is provided to reflector 502 by a motor 704 with an eccentric cam 704a. The location of reflector 502 is sensed by a position sensor 706. The reflected light pattern size is determined by sensor 702. Signals from sensors 702, 706 are directed to a processor 708 which generates a signal indicating pattern size as a function of reflector position. This can also be used by the processor to evaluate for errors in lens curvature. A graph of a typical output signal is shown in FIG. 7 as pattern size versus the position of reflector 502. Thus, in the apparatus of FIG. 6, a fixed light beam is used and the position of reflector 502 altered to evaluate the pattern.

Figures 8, 9:
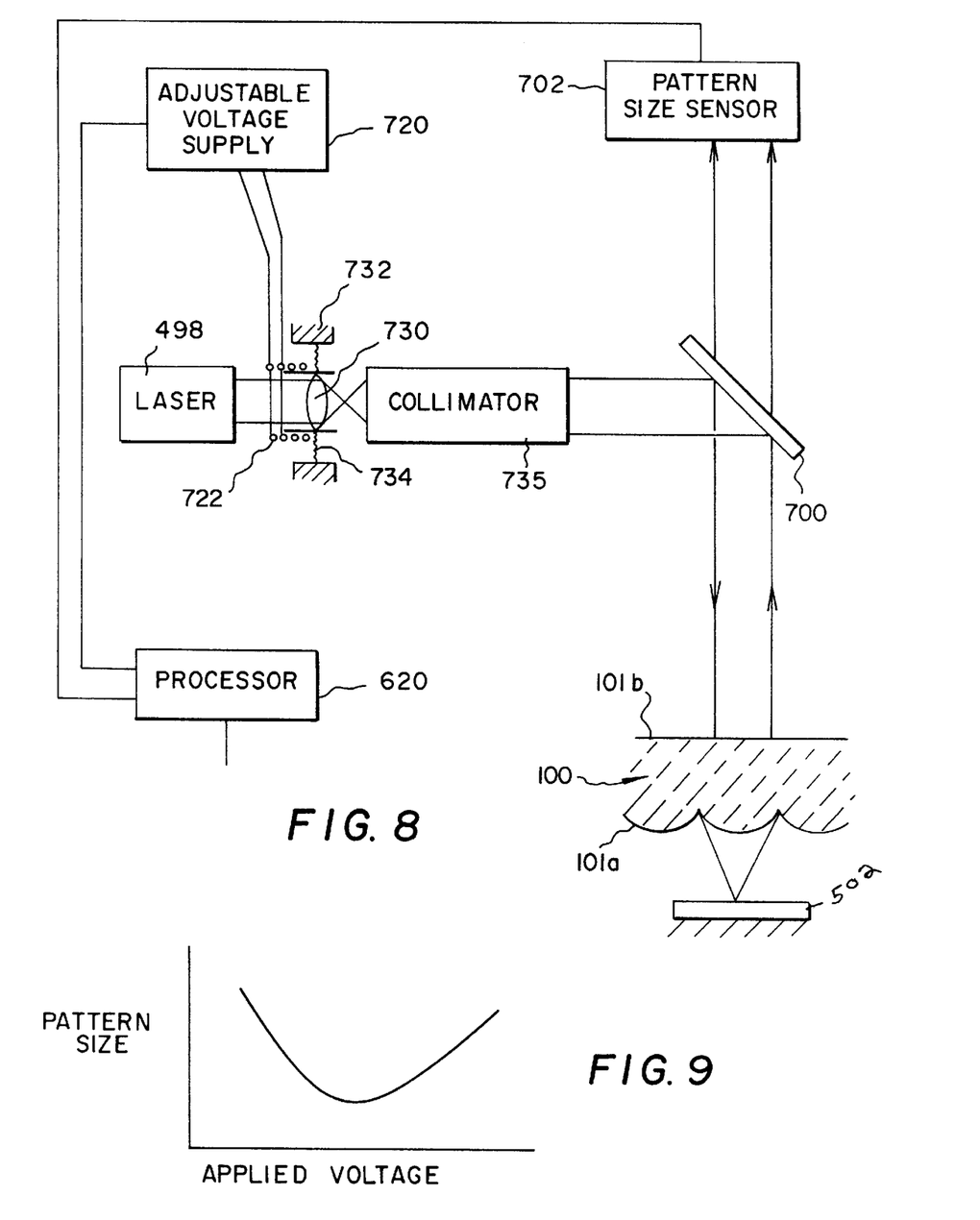
FIG. 8 is a schematic diagram showing an alternative apparatus to that of FIG. 6.
FIG. 9 is a graph of a signal output by the apparatus of FIG. 9.

Referring to FIG. 8, an alternative apparatus to that of FIG. 6 is shown. In the apparatus of FIG. 8 the function of the oscillating the reflector 502 is replaced by oscillation of a different optical element. Thus, in FIG. 8 a fixed reflector 502 is used and the location at which the light beam from a laser 498 focuses after passing through lens sheet 101 is altered to evaluate the reflected pattern. In particular, in FIG. 8, a variable voltage is applied from power supply 720 to a magnetic coil 722 which repositions a lens 730 against a tension of a spring 734. Spring 734 is connected to a frame 732. As lens 730 is repositioned relative to a collimator 735, convergence of the nominally collimated light beam emerging from collimator 735 is altered thereby causing the location of the focused line of light to change relative to the front surface 101a. The magnitude of the voltage from supply 720 and the pattern size detected at sensor 702, are fed to processor 708. Processor 620 generates a signal such as illustrated in FIG. 9, showing pattern size versus voltage applied to coil 722. After previously calibrating the relationship between voltage applied to coil 722 to focus location of the line, this signal is used by processor 620 to determine changes to the lens sheet forming process to reduce the pattern size at sensor 702 to an acceptable (preferably minimum possible) value for a collimated input light beam.

Figure 10:
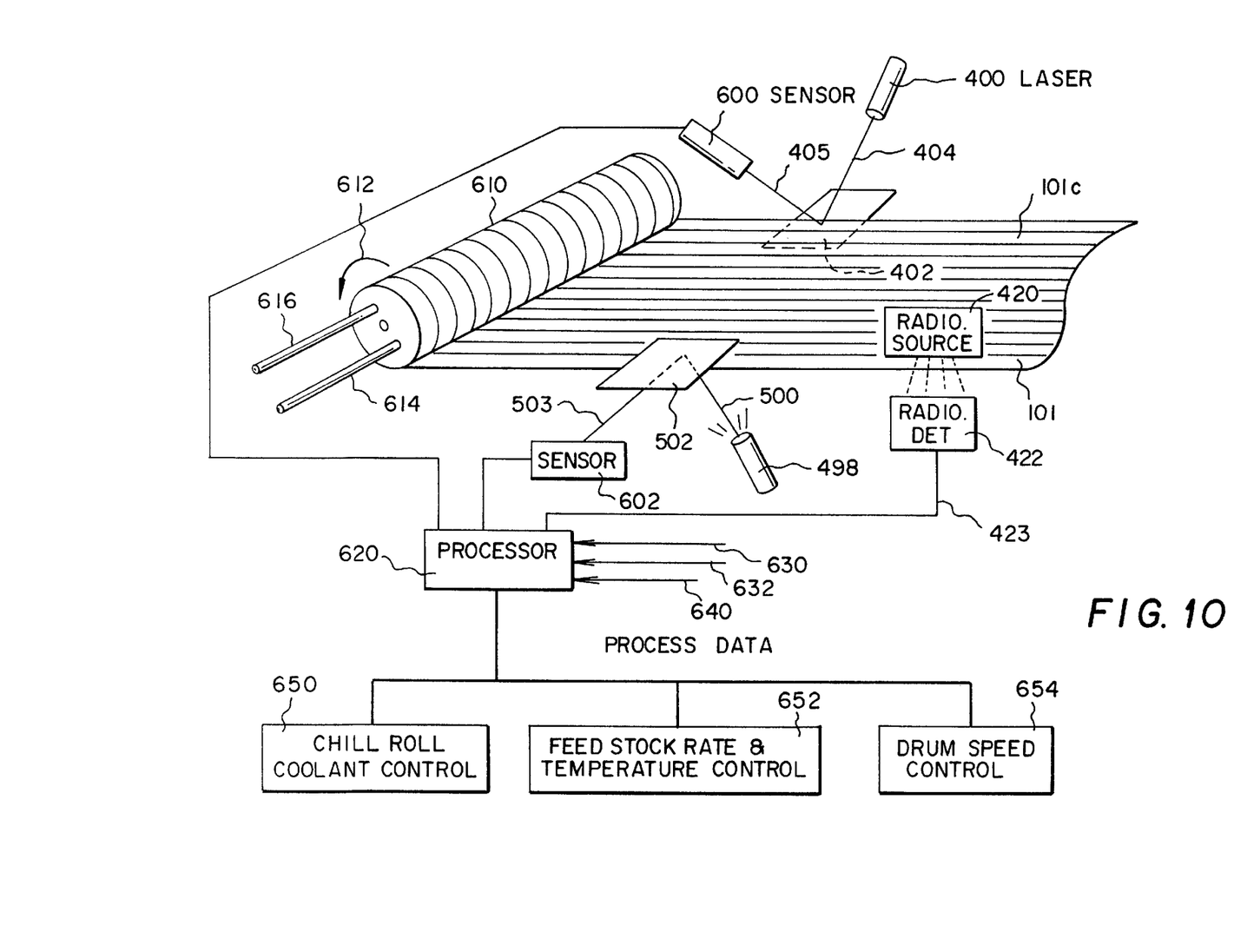
FIG. 10 schematically shows a lenticular lens manufacturing apparatus of the present invention.

FIG. 10 shows a particular embodiment of the present invention as used to manufacture lenticular lens sheet using an extrusion process. By employing simultaneous evaluations of reflected laser beams from both sides of the sheet, feedback signals are generated to change extrusion parameters under a limiting control based on actual simultaneous measurement of lens sheet thickness. These feedback signals are generated using the simultaneous evaluations and lookup tables which are either empirically determined or determined from direct engineering calculations. Such an arrangement is shown in the lenticular sheet forming apparatus of FIG. 10. In FIG. 10, a lens sheet forming apparatus includes a chill roller 610 carrying a series of partially cylindrical adjacent parallel, circularly extending grooves along its surface. These grooves correspond to the lens surfaces 101c which they will form. Chill roller 610 is provided with a metered flow of molten lens plastic from a sheet die (not shown), and has its temperature controlled by water flowing through inlet and outlet water conduits 614, 616 which water is at a temperature below the melting point of the lens plastic. Chill roller 610 is rotated at a controlled speed in the direction of arrow 612 by a motor (not shown), all in a known manner. As a result a continuous lens sheet 101 is formed with the lenticules 101c extending in a direction parallel to the output direction which is normal to the axis of chill roller 610. The front side 101a of sheet 101 faces upward as seen in FIG. 10. A quality analyzer uses a first laser light source 400, reflector 402 positioned behind back side 101b of sheet 101, as described in connection with FIG. 4. A first sensor 600, which may be an area Charge Coupled Device ("CCD") sensor, detects the size of pattern 406. Similarly, the quality analyzer includes a second laser light source 498 positioned to illuminate lens sheet 101 from the back side 101b in the manner shown in connection with FIGS. 5A–5C, with beam 503a, 503b, 503c being reflected off mirror 502 forward of the front side 101a in the manner shown in connection with FIGS. 5A–5C and passing back through the back side 101b. Alternatively, the arrangement of FIG. 8 could be used instead of that of FIGS. 5A–5C. In FIG. 10 a second sensor 602 detects the width of the pattern of beam 503. Signals from first and second sensors 600, 602 are digitized and fed to processor 620. Processor 620 can be a general purpose digital computer suitably programmed to execute the required steps, although it can, of course, be equivalent hardware elements or a combination of hardware and software. Processor 620 receives data inputs such as on lines 630, 632, 640 which provide sensed process parameters from sensors (not shown), such as the temperature of chill roller 610, the feed rate of the molten plastic and its temperature, and the rotational speed of chill roller 610. Processor 620 compares an observed feature of the data received from sensors 600, 602 (which is the width of the patterns, as discussed in connection with FIGS. 4, 5A–5C) with a corresponding reference feature (such as the ideal widths of the respective patterns sensed on sensors 600, 602, respectively). The internal comparison are first and second comparison signals. Other features which may be used in addition or instead of the width, include light intensity distribution within the reflected pattern. Also, when the width of the pattern is used, this width can be defined as the distance between the two locations on the pattern at which light intensity drops below a predetermined lower limit. Processor 620 is also provided with data (look-up tables) which indicates how controlled process parameters should be varied depending on the values of the foregoing two comparisons. Such data can be obtained from previously conducted empirical tests. Additionally, a secondary measurement of lenticular lens sheet thickness is provided to processor 620. This is provided by a prior art method using a radioactive source 420 and a radioactivity detector 422 providing signal 423, all in a known manner. From signal 423 processor 620 can determine lens sheet thickness. From the data signals from sensors 600, 602 then, processor 620 can determine which controlled parameter or parameters needs to be varied to improve the quality of the lens sheet 101 which will be produced from roller 610. However, if the first and second comparison signals deviate beyond predetermined limits, or the desired lens sheet thickness change from processor 620 exceeds preset ranges of allowed thickness which is actively measured by detector 422, different corrective control signals, such as an operator intervention warning, can be programmed in processor 620. Corresponding control data is then generated by controller 620, such as chill roll coolant control data 650, molten plastic feed stock rate 652, and chill roller speed control data 654. This data is fed to suitable controlling mechanisms (not shown) for the each of the foregoing items.

In this forgoing discussion, the size of the collimated beam diameter relative to the pitch of the lenticular material was not mentioned. In experiments run, the beam diameter has been found to work satisfactorily even when its diameter encompasses 5 to 10 adjacent lenticules versus just one lenticule. If the distance from the sheet under test to the screen location is kept quite large (over 1000 beam diameters or more), the patterns of single lenticule performance and multiple adjacent lenticule performances are very similar. Beams of larger diameter are easier to align and sense and therefore would be preferably employed.

It should also be noted that any of the reflecting surfaces described above, rather than being perfectly specular, may usefully be a somewhat diffuse reflector. For example, the reflecting surface may reflect about 20% of the light in a non-specular manner.

The invention has been described in detail with particular reference to certain preferred embodiments thereof, but it will be understood that variations and modifications can be effected within the spirit and scope of the invention.

PARTS LIST

100 Collimated beam of light
101 Lenticular sheet
101a Front side of sheet
101b Planar back side
101c Lens surface
102 Microscope
103 User's eye
200 Collimated light beam
202 Flat reflective surface
203a, 203b, Rays of light
203c 203d
204a, 204b, Emerging rays
204c 204d
205a, 205b, Normals
205c, 205d
300i, 300ii, Paths
302
306 Line
306i, 306ii, Paths
306iii, 306iv
307 Line
307i, 307ii Paths
400 Helium-neon type laser
402 Planar reflector
404 Input beam
405 Reflected beam
406 Pattern
407 Screen
408 Axis
409 Direction arrows
420 Radioactive source
422 Radioactivity detector
423 Signal
498 Llaser light source
500 Ray
502 Reflector
502a Front surface
503 Beam
503a, 503b, Rays
503c
504 Direction of oscillation
600 Sensor
602 Sensor
610 Chill roller
612 Arrow
614,616 Water conduits
620 Processor
630,632, Data lines
640
650 Chill roll coolant control data
652 Molten plastic feed stock rate 654 Chill roller speed control data
700 Beam splitter
702 Sensor
704 Motor
704a Eccentric cam
706 Position sensor
720 Power supply
722 Magnetic coil
730 Lens
732 Frame
734 Spring
735 Collimator

We claim:

1. A method of evaluating the quality of a lenticular lens sheet having a front side carrying a plurality of elongated parallel lens elements having a pitch between lens elements, and a back side, comprising:
   (a) illuminating the sheet from one of the sides with a collimated light beam having a width at least equal to or greater than said pitch between lens elements so that the light passes through the sheet and is then reflected from a reflector behind the other side to pass back through the sheet; and
   (b) comparing an observed feature of a pattern of the reflected light which has passed back through the sheet with a corresponding reference feature to provide an indication of the lenticular lens sheet quality.

2. A method according to claim 1 wherein the front side of the lenticular lens sheet is illuminated with the collimated light source, and the reflector is positioned behind the back side.

3. A method according to claim 2 wherein the back side of the lenticular lens sheet is nominally flat.

4. A method according to claim 2 wherein the reflector is positioned in contact with the back side of the lens sheet.

5. A method according to claim 1 wherein the distance between the lens sheet and the reflector is varied while comparing the observed feature of the pattern.

6. A method according to claim 1 wherein the distance between the lens sheet and reflector is varied until the difference between the observed and reference features is minimized.

7. A method according to claim 1 wherein the distance between the lens sheet and reflector is varied between known values and the variation of the observed feature is observed to provide an indication of a required thickness change to the lenticular sheet.

8. A method according to claim 1 the feature compared comprises an observed pattern width with a reference pattern width.

9. A method according to claim 1 wherein the lens sheet is illuminated with a beam in plane normal to the sheet and parallel to the axis of the lenticule.

10. A method of evaluating the quality of a lenticular lens sheet having a front side carrying a plurality of elongated parallel lens elements, and a back side, comprising:
    (a) illuminating the sheet from the front side with a collimated light source so that the light passes through the sheet and is then reflected from a reflector behind the back side to pass back through the sheet;
    (b) comparing an observed feature of a pattern of the reflected light which has passed back through the sheet with a corresponding first reference feature to provide an indication of the lenticular lens sheet quality;
    (c) illuminating the sheet from the back side with a collimated light source so that the light passes through the sheet and is then reflected from a reflector forward of the front side to pass back through the sheet; and
    (d) comparing an observed feature of a pattern of the reflected light which has passed back through the sheet with a corresponding second reference feature to provide an indication of the lenticular lens sheet quality.

11. A method according to claim 10 wherein the comparison of step (b) provides an indication of lens sheet thickness.

12. A method according to claim 10 wherein the comparison of step (d) provides an indication of lens shape.

13. A method according to claim 10 wherein steps (a) through (d) are performed on the same lens sheet simultaneously.

14. A method according to claim 10 wherein, in steps (a) and (c), the lens sheet is illuminated at an angle to a normal to the sheet, with the direction of illumination and the direction of the observed feature in steps (b) and (d), respectively, being in a plane normal to the sheet and parallel to the axis of the lenticule.

15. A method of manufacturing a continuous lenticular lens sheet having a front side carrying a plurality of elongated parallel lens elements, and a back side, comprising:
    (a) forming the continuous lenticular lens sheet;
    (b) evaluating the quality of the formed lenticular lens sheet by:
        (i) illuminating the sheet from one of the sides with a light source so that the light passes through the sheet and is then reflected from a reflector behind the other side to pass back through the sheet; and
        (ii) comparing an observed feature of a pattern of the reflected light which has passed back through the sheet with a corresponding reference feature to provide an indication of the lenticular lens sheet quality;
        (iii) generating a comparison signal corresponding to the results of the comparison of step (ii);
    (c) automatically adjusting the conditions under which the continuous lens sheet is formed in response to the comparison signal.

16. A method of manufacturing a continuous lenticular lens sheet having a front side carrying a plurality of elongated parallel lens elements, and a back side, comprising:
    (a) forming the continuous lenticular lens sheet;
    (b) evaluating the quality of the formed lenticular lens sheet by:
        (i) illuminating the sheet from the front side with a light source so that the light passes through the sheet and is then reflected from a reflector behind the back side to pass back through the sheet;
        (ii) comparing an observed feature of a pattern of the reflected light which has passed back through the sheet with a corresponding first reference feature to provide an indication of the lenticular lens sheet quality;
        (iii) generating a first comparison signal corresponding to the results of the comparison of step (ii);
        (iv) illuminating the sheet from the back side with a light source so that the light passes through the sheet and is then reflected from a reflector forward of the front side to pass back through the sheet;
        (v) comparing an observed feature of a pattern of the reflected light which has passed back through the sheet with a corresponding second reference feature to provide an indication of the lenticular lens sheet quality; and
        (vi) generating a second comparison signal corresponding to the results of the comparison of step (v); and (c) automatically adjusting the conditions under which the continuous lens sheet is formed so that the thickness of the lens sheet is altered in response to the first comparison signal, and so that the lens shapes are altered in response to the second comparison signal.

17. A method according to claim 16 wherein when the first and second comparison signals deviate beyond predetermined limits, an operator intervention signal is generated.

18. An apparatus for evaluating the quality of a lenticular lens sheet having a lenticular element pitch, having:
   (a) a collimated light beam having a width at least equal to or greater than said lenticular element pitch to illuminate the sheet from one of the sides;
   (b) a reflector positioned to be behind the other side of the lens sheet so that the light from the light source can pass through the sheet and is then reflected from the reflector to pass back through the sheet; and
      (iii) a first sensor to detect a feature of a pattern of the reflected light which has passed back through the sheet; and
      (iv) a first comparator to compare the feature detected by the first sensor with a corresponding reference feature and generate a first comparison signal.

19. An apparatus according to claim 18 additionally comprising means to vary the distance between the reflector and the lens sheet.

20. An apparatus for manufacturing a lenticular lens sheet having a front side carrying a plurality of elongated parallel lens elements, and a back side, the apparatus comprising:
   (a) a lens sheet forming apparatus to form the lenticular lens sheet, the apparatus including parameter controlling means for varying at least one lens forming parameter in response to a comparison signal which provides an indication of the lenticular lens sheet quality;
   (b) a quality analyzer to evaluate the quality of the formed lenticular lens sheet, having:
      (i) a light source to illuminate the sheet from one of the sides;
      (ii) a reflector positioned behind the other side of the lens sheet so that the light from the light source passes through the sheet and is then reflected from the reflector to pass back through the sheet; and
      (iii) a first sensor to detect a feature of a pattern of the reflected light which has passed back through the sheet;
      (iv) a first comparator to compare the feature detected by the first sensor with a corresponding reference feature and generate the first comparison signal.

21. An apparatus according to claim 20 additionally comprising means for varying the distance between the reflector and lens sheet.

22. An apparatus according to claim 20 additionally comprising an auxiliary thickness sensor which provides an indication of lenticular lens sheet thickness to verify lens sheet thickness changes are within predetermined limits.

* * * * *